US00PP10526P

United States Patent [19]

Pounders, Jr.

[11] Patent Number: Plant 10,526

[45] Date of Patent: Jul. 28, 1998

[54] ILEX HYBRID VARIETY NAMED 'XIA XIANG'

[76] Inventor: Cecil T. Pounders, Jr., 3140 Old Moulton Rd., Decatur, Ala. 35603

[21] Appl. No.: 842,474

[22] Filed: Apr. 23, 1997

[51] Int. Cl.[6] ..... A01H 5/00

[52] U.S. Cl. ..... Plt./65

[58] Field of Search ..... Plt./65

*Primary Examiner*—James R. Feyrer
*Assistant Examiner*—Kent L. Bell

[57] ABSTRACT

A new and distinct variety of evergreen holly which is particularly distinguished in that it combines desirable landscape and production traits from two species, *Ilex myrtifolia* and *Ilex opaca*, which distinguish it from all other forms of Ilex. Plants have a densely branched compact pyramidal crown with fine textures deep green leaves. Pistillate flowers are borne abundantly on initial spring shoots giving a well distributed fruit set. Berries mature to a colorful red in the early fall then persist throughout the winter.

2 Drawing Sheets

SUMMARY OF THE INVENTION

My invention is new, distinctive and useful form of Ilex originated by me by selection of a superior seeding from a group of open pollinated seedlings of *Ilex myrtifolia×opaca* 'Tanager', an unpatented variety.

The objective of my breeding was to create a hardy versatile decorative shrub which combined the texture and compact growth habit of *Ilex myrtifolia* with the hardiness and versatility of *Ilex opaca*. This invention comprises a novel combination of traits from the two species which distinguish it from all over forms of Ilex of which I am aware. The new clone has been named the 'Xia Xiang' variety.

The following combination of traits is exhibited by the variety:

(a) densely branched, vigorous, symmetrical crown requiring minimal shearing,
(b) compact, upright growth habit with strong apical dominance,
(c) adapted to a wide range of landsacpe environments,
(d) evergreen minutely spine tipped serrulate leaves which are borne on branches that become pendulous when plants are not sheared,
(e) pistillate flowers borne abundantly on initial spring shoots,
(f) well distributed fruit set with berries maturing to a colorful red in the early fall then persisting throughout the winter,
(g) cold hardiness, heat and drought tolerance equivalent to *Ilex opaca*.

'Xia Xiang' variety was selected as a replacement for *Ilex×attenuata* 'Foster 2' in the landscape. Foster holly is planted extensively in the southern United States but has a number of inferior traits such as lack of crown symmetry and poor apical dominance without frequent extensive shearing during production. Production trials comparing 'Xia Xiang' holly to Foster holly reveal that the self-branching apical dominant growth habit of 'Xia Xiang' reduces pruning expenses and the number of culls as compared to Foster holly. Improvements over the female parent, 'Tanager', include strong apical dominance of the plant's central leader, more symmetrical crown development without extensive shearing, greener foliage and improved environmental tolerance to cold, drought and heat.

Asexual propagation of my new variety by cutting has been accomplished at Decatur, Ala. and Loxley, Ala. It has been demonstrated that the unique combination of characteristics has been established and transmitted to successive generations.

It is anticipated that the new cultivar will be marketed while bearing the DIXIE DREAM HOLLY trademark.

BRIEF DESCRIPTION OF THE PHOTOGRAPHS

The accompanying photographs show typical specimens of my new variety of Ilex during fall and early winter as depicted in color as true as is reasonably possible to make the same in color photographs of the character. The specimens illustrated were being grown in the ground at Decatur, Ala. and in containers at Loxley, Ala.

DETAILED DESCRIPTION

Figure 1:
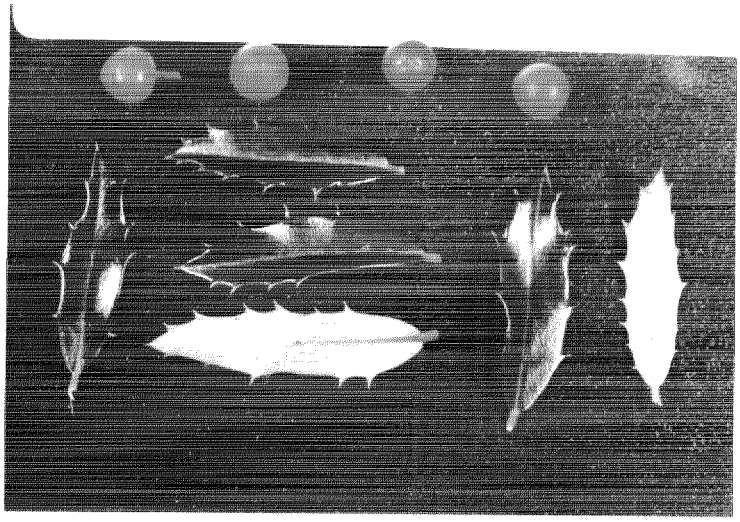
FIG. 1 illustrates fruit and foliage shape, size and color.
Figure 2:
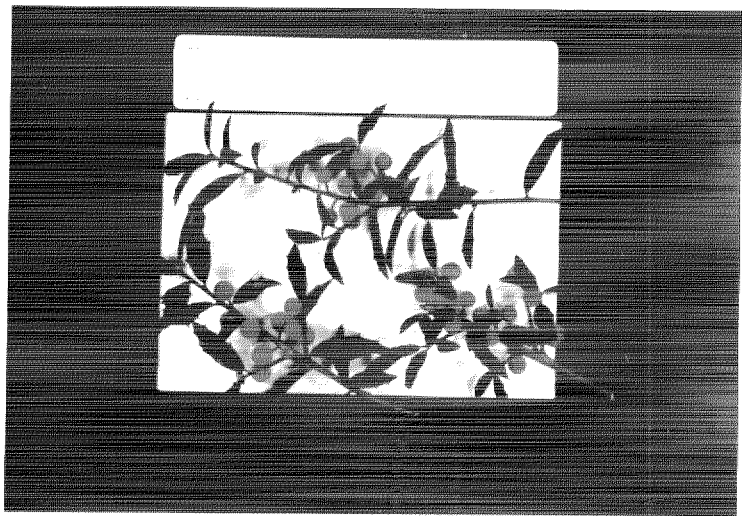
FIG. 2 illustrates fruit set within foliage samples.
Figure 3:
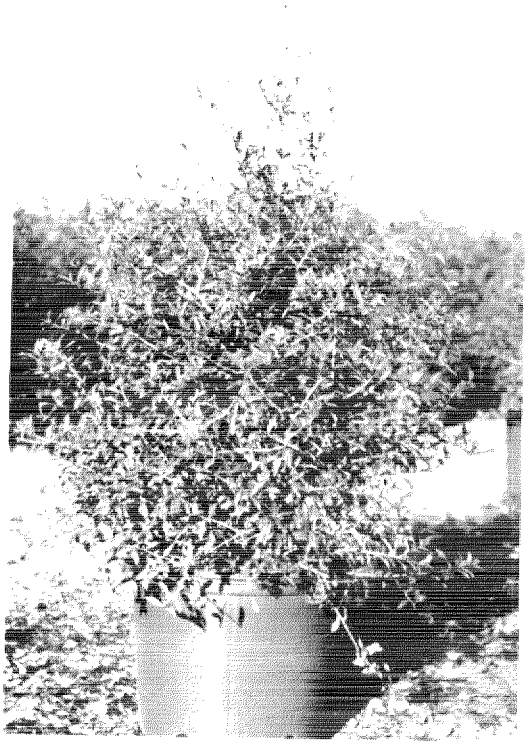
FIG. 3 illustrates uniformity of variety in a production environment.

The following is a detailed description of my new variety of Ilex made from observation of plants growing in the ground at Decatur, Ala. Color terminology is in accordance with the R.H.S. Colour Chart of The Royal Horticultural Society, London, England.

Parentage: Open pollinated seedling of *Ilex myrtifolia× opaca* 'Tanager'.

Foliage:

*Type.*—Evergreen, coriaceous, semi-glossy. Leaves primarily oblanceolate, remotely serrulate with minute spine-tipped teeth, often revolute.

*Size.*—Leaf size varies with light intensity and fertility program where plants are growing. Size is generally in the range of 3–5 cm long and 0.5–1.5 cm wide.

*Petiole.*—Approximately 2 to 5 mm.

*Color.*—Mature leaves, upper surface is closest to Green Group 133A; under surface ranges from Yellow Green Group 144A to Yellow Green Group 153D as leaf orientation to sunlight varies. Petiole and midrib, varying degrees of red coloration.

Stems:

*Color.*—On new growth stems are Purple Group 79A then mature to Grey Brown Group 199C.

Flowering: Flowers are pistillate and typical of the genus in morphology and timing. Flowers are not seen to be particularly distinguishing.

Fruit:

*Color.*—Dull to Semi-glossy, Red Group 44A.

*Size.*—Drupe, globose to slightly ellipsoid, approximately 5 mm.

Plant growth characteristics: Plants have a compact pyramidal habit of growth with six year individuals attaining a size of approximately 2 m in height and 0.7 m in breadth at the base. Crowns are dense and uniform with minimum shearing. Trunks have a silver gray appearance and when exposed provide a nice contrast to the green foliage and red fruit.

I claim:

1. A new and distinct variety of Ilex plant, substantially as herein shown and described, characterized particularly as to novelty by the unique combination of:

(a) a vigorous densely branched shrub with a symmetrical crown with only minimal shearing, (b) compact, upright growth habit with strong apical dominance, adapted to a wide range of landscape applications, (c) evergreen minutely spine tipped serrulate deep green leaves which are borne on branches that become pendulous when plants are not sheared, (d) pistillate flowers borne abundantly on initial spring shoots giving a well distributed fruit set with berries maturing to a colorful red in the early fall then persisting throughout the winter, (e) cold hardiness, heat and drought tolerance equivalent to *Ilex opaca*.

* * * * *